US010527690B2

(12) United States Patent
Kim

(10) Patent No.: US 10,527,690 B2
(45) Date of Patent: Jan. 7, 2020

(54) RADIO FREQUENCY COIL FOR MAGNETIC RESONANCE IMAGING, MAGNETIC RESONANCE IMAGING SYSTEM, AND METHOD OF GENERATING IMAGE OF MAGNETIC RESONANCE IMAGING SYSTEM

(71) Applicant: Samsung Electronics Co., Ltd., Suwon-si (KR)

(72) Inventor: Kyoungnam Kim, Incheon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 240 days.

(21) Appl. No.: 15/317,722

(22) PCT Filed: Jun. 29, 2015

(86) PCT No.: PCT/KR2015/006618
§ 371 (c)(1),
(2) Date: Dec. 9, 2016

(87) PCT Pub. No.: WO2016/003128
PCT Pub. Date: Jan. 7, 2016

(65) Prior Publication Data
US 2017/0139019 A1     May 18, 2017

(30) Foreign Application Priority Data

Jun. 30, 2014  (KR) .......................... 10-2014-0081211

(51) Int. Cl.
*G01R 33/36*   (2006.01)
*G01R 33/34*   (2006.01)

(52) U.S. Cl.
CPC .............................. *G01R 33/34046* (2013.01)

(58) Field of Classification Search
CPC .. G01R 33/36; G01R 33/546; G01R 33/3415; G01R 33/3692
USPC .......................................... 324/301, 302, 304
See application file for complete search history.

(56) References Cited

U.S. PATENT DOCUMENTS

| 4,793,356 A | 12/1988 | Misic et al. |
| 7,733,088 B2 | 6/2010 | Cho et al. |
| 2002/0089329 A1 | 7/2002 | Harvey et al. |
| 2005/0146327 A1* | 7/2005 | Jakab ................... G01R 33/285 324/302 |
| 2005/0237056 A1* | 10/2005 | Nabetani ............ G01R 33/3415 324/302 |

(Continued)

FOREIGN PATENT DOCUMENTS

| KR | 10-2004-0013705 A | 2/2004 |
| KR | 10-2009-0053181 A | 5/2009 |
| KR | 10-2012-0015580 A | 2/2012 |

OTHER PUBLICATIONS

International Search Report dated Sep. 17, 2016, in counterpart International Application No. PCT/KR2015/006618 (3 pages in English, 4 pages in Korean).

(Continued)

*Primary Examiner* — Patrick Assouad
*Assistant Examiner* — Taqi R Nasir
(74) *Attorney, Agent, or Firm* — NSIP Law

(57) ABSTRACT

Disclosed is a radio frequency (RF) coil for magnetic resonance imaging (MRI), the RF coil including: a bow-tie antenna; and a loop coil.

14 Claims, 5 Drawing Sheets

(56) References Cited

U.S. PATENT DOCUMENTS

| | | | | |
|---|---|---|---|---|
| 2006/0091881 A1* | 5/2006 | Clarke | ................. | G01R 33/326 |
| | | | | 324/301 |
| 2006/0172556 A1* | 8/2006 | Bather | ................. | C23C 16/345 |
| | | | | 438/794 |
| 2006/0192556 A1* | 8/2006 | Harvey | .............. | G01R 33/3854 |
| | | | | 324/318 |
| 2008/0157772 A1* | 7/2008 | Okamoto | ........... | G01R 33/3415 |
| | | | | 324/322 |
| 2008/0180091 A1* | 7/2008 | Kakuya | ................ | G01D 5/2006 |
| | | | | 324/207.16 |
| 2009/0134873 A1* | 5/2009 | Cho | ................. | G01R 33/34046 |
| | | | | 324/318 |

OTHER PUBLICATIONS

International Search Report dated Sep. 17, 2015, in counterpart International Application No. PCT/KR2015/006618 (3 pages in English, 4 pages in Korean).

\* cited by examiner (a)   (b)   (c)   (d)   (e)

RADIO FREQUENCY COIL FOR MAGNETIC RESONANCE IMAGING, MAGNETIC RESONANCE IMAGING SYSTEM, AND METHOD OF GENERATING IMAGE OF MAGNETIC RESONANCE IMAGING SYSTEM

CROSS REFERENCE TO RELATED APPLICATIONS

This application is a National Phase entry of PCT Application No. PCT/KR2015/006618, filed on Jun. 29, 2015, which claims priority under 35 U.S.C. § 119(e), 120 and 365(c) to Korean patent application no. 10-2014-0081211, filed on Jun. 30, 2014, in the Korean Intellectual Property Office, the entire disclosures of each of which are incorporated herein by reference for all purposes.

TECHNICAL FIELD

One or more embodiments of the present disclosure relate to a radio frequency (RF) coil for magnetic resonance imaging (MRI), an MRI system, and a method of generating an image of the MRI system.

BACKGROUND ART

A magnetic resonance imaging (MRI) device, a magnetic resonance spectroscopy (MRS) device, and the like have been well known as an MRI system using nuclear magnetic resonance (NMR) phenomena.

An MRI device captures images of cross-sections of a human body by using NMR phenomena. Since atomic nucleuses such as hydrogen (1H), phosphorous (31P), sodium (23Na), and carbon isotopes (13C) existing in a human body each have a unique rotating field that is constant due to the NMR phenomena, a high frequency is applied to magnetization vectors of the atomic nucleuses, which are arranged in a direction of a main magnetic field, by using an RF coil, and the images of the cross-sections of the human body may be obtained as the RF coil receives a magnetic resonance signal generated when the magnetization vectors are rearranged on a vertical plane due to frequency resonance.

The RF coil includes an RF antenna that transmits a high frequency and receives a magnetic resonance signal to resonate the magnetization vectors. The resonance of the magnetization vectors by using one RF coil (the RF antenna) (i.e., an RF transmission mode) and receiving the magnetic resonance signal (i.e., an RF receiving mode) may be simultaneously performed. Alternatively, an RF coil only for the RF transmission mode and an RF coil only for the RF receiving mode are separately used to separately perform the RF transmission mode and the RF receiving mode. A coil that performs both the RF transmission mode and the RF receiving mode is referred to as a transmit/receive (Tx/Rx) coil. A Tx-only coil is referred to as a transmission coil, and an Rx-only coil is referred to as a receiving coil.

DETAILED DESCRIPTION OF THE INVENTION

Technical Problem

One or more embodiments of the present disclosure provide a radio frequency (RF) coil for magnetic resonance imaging (MRI), an MRI system, and a method of generating an image of the MRI system. Technical problems are not limited to the technical problems described herein, and there may be other technical problems.

Technical Solution

According to one or more embodiments, a radio frequency (RF) coil for magnetic resonance imaging (MRI), includes: a bow-tie antenna; and a loop coil.

The RF coil may include a plurality of loop coils, and the bow-tie antenna may be between the plurality of loop coils.

The RF coil may include a plurality of bow-tie antennas, and the plurality of bow-tie antennas and the plurality of loop coils may be alternately aligned.

The bow-tie antenna may include two triangle portions that are symmetrical to each other, and vertices of the two triangle portions may point to a central portion of the bow-tie antenna.

The loop coil may be polygonal, the loop coil may be close to the bow-tie coil, and a vertex of the loop coil may point to the central portion of the bow-tie antenna.

The RF coil may include a plurality of bow-tie antennas, the loop coil may be between the plurality of bow-tie antennas, and vertices of the loop coil may respectively point to central portions of the plurality of bow-tie antennas arranged around sides of the loop coil.

The loop coil may be adjacent to the bow-tie coil and be parallel to an edge of one of the two triangle portions.

The bow-tie antenna may include a first triangle portion and a second triangle portion, the loop coil may include a first line segment parallel to an edge of the first triangle portion and a second line segment parallel to an edge of the second triangle portion, and a vertex between the first and second line segments may point to a central portion of the bow-tie antenna.

The bow-tie antenna may transmit an RF signal, and the loop coil may receive, from a subject, a magnetic resonance signal resulting from excitation by the RF signal.

The loop coil may operate in a transmission mode in which the RF signal is transmitted or in a receiving mode in which the magnetic resonance signal resulting from the excitation by the RF signal is received from the subject.

Each of the bow-tie antenna and the loop coil may be connected to an RF channel.

The bow-tie antenna and the loop coil may be in a horizontal direction on a same plane.

According to one or more embodiments, a magnetic resonance imaging (MRI) system includes: a radio frequency (RF) coil configured to transmit an RF signal to a subject and obtain a magnetic resonance signal from a region of interest of the subject, the magnetic resonance signal resulting from excitation by the transmitted RF signal; an RF coil controller configured to an RF transmission mode and an RF receiving mode of the RF coil; and an image processor configured to generate an MRI image of the subject based on the obtained magnetic resonance signal, wherein the RF coil comprises a bow-tie antenna and a loop coil.

According to one or more embodiments, a method of generating an image of a magnetic resonance imaging (MRI) system including a radio frequency (RF) coil including a bow-tie antenna and a loop coil, the method includes: transmitting an RF signal to a subject by using the bow-tie antenna; obtaining a magnetic resonance signal from a region of interest of the subject by using the loop coil, the magnetic resonance signal resulting from excitation by the transmitted RF signal; and generating an MRI image of the subject based on the obtained magnetic resonance signal.

The loop coil may operate in a transmission mode in which the RF signal is transmitted or in a receiving mode in which the magnetic resonance signal resulting from excitation by the RF signal is received from the region of interest of the subject, and in the transmitting of the RF signal, the RF signal may be transmitted to the subject by using the bow-tie antenna and the loop coil.

These and/or other aspects will become apparent and more readily appreciated from the following description of the embodiments, taken in conjunction with the accompanying drawings.

Advantageous Effects of the Invention

According to a radio frequency (RF) coil for magnetic resonance imaging (MRI), an MRI system, and a method of generating an image of the MRI system, an RF coil structure, which has improved sensitivity and homogeneity in a B1 field of a region of interest and great decoupling performance, is provided.

BEST MODE

Figure 1A:
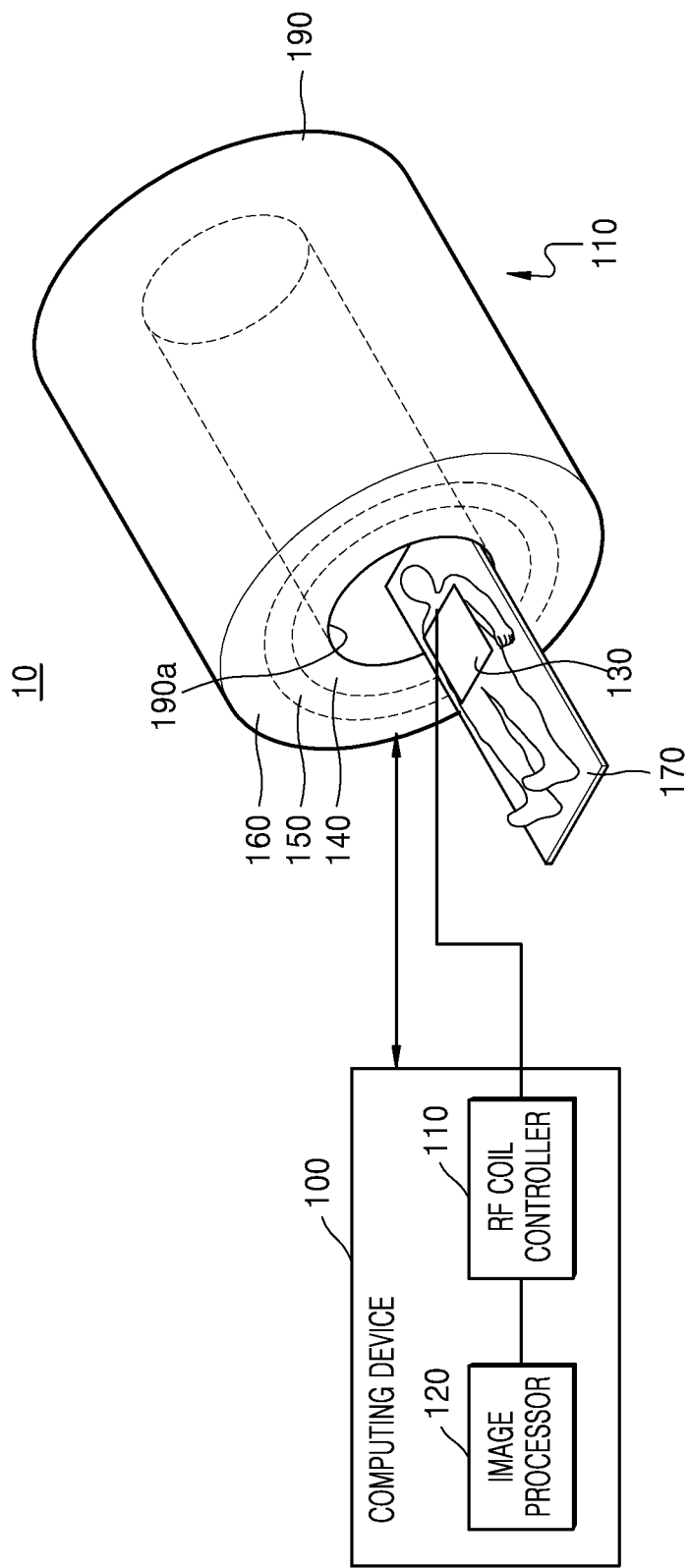
FIGS. 1A and 1B are structural diagrams of a magnetic resonance imaging (MRI) system 10 according to an embodiment.

As the present disclosure allows for various changes and numerous embodiments, particular embodiments will be illustrated in the drawings and described in detail in the written description. The attached drawings for illustrating embodiments of the present disclosure are referred to in order to gain a sufficient understanding of the present disclosure, the merits thereof, and the objectives accomplished by the implementation of the present disclosure. The present disclosure may, however, be embodied in many different forms and should not be construed as being limited to the embodiments set forth herein.

Hereinafter, the present disclosure will be described in detail by explaining embodiments of the invention with reference to the attached drawings. Like reference numerals in the drawings denote like elements.

An expression used in the singular encompasses the expression of the plural, unless it has a clearly different meaning in the context. In the present specification, it is to be understood that the terms such as "including", "having", and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Sizes of components in the drawings may be exaggerated for convenience of explanation. In other words, since sizes and thicknesses of components in the drawings are arbitrarily illustrated for convenience of explanation, the following embodiments are not limited thereto.

Figure 1B:
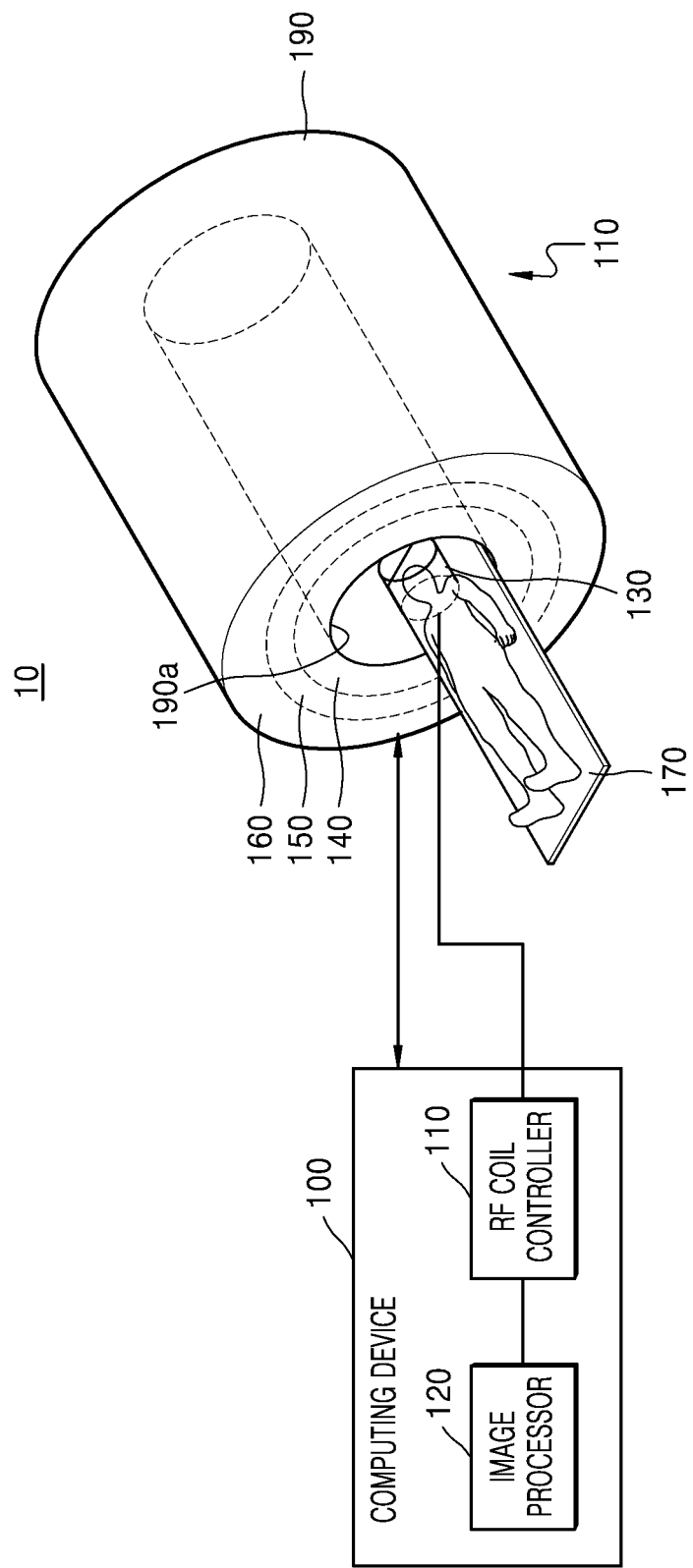

FIGS. 1A and 1B are structural diagrams of a magnetic resonance imaging (MRI) system 10 according to an embodiment.

Referring to FIGS. 1A and 1B, shapes of a radio frequency (RF) coil assembly 130 are different as planar and cylindrical structures, but other elements thereof are the same. Hereinafter, the RF coil assembly 130 will be described with reference to both FIG. 1A and FIG. 1B. Referring to FIGS. 1A and 1B, the MRI system 10 includes a computing device 100 and a cylindrical housing 190.

The cylindrical housing 190 includes a transmit (Tx) only volume-type RF coil device 140, a gradient coil 150, and a main magnet 160 in a stated order from the inside of the cylindrical housing 190 to the outside thereof. A subject lying on a table 170 is moved to a hollow hole 190a of the cylindrical housing 190, and then an MRI image is captured.

In the MRI system 10, the Tx only volume-type RF coil device 140, the gradient coil 150, and the main magnet 160 of the cylindrical housing 190 are connected to the computing device 100 and then driven and controlled by the computing device 100. The computing device 100 may be connected to a console (not shown) used to display the captured MRI image of the subject or receive a manipulation signal of a user.

In the MRI system 10, the Tx only volume-type RF coil device 140 may be independently driven or controlled by an RF coil controller 110 of the computing device 100 together with the RF coil assembly 130 of FIGS. 1A and 1B installed on a body portion of the subject that is to be subjected to examination. Hereinafter, the term 'RF coil' denotes the RF coil assembly 130 according to an embodiment.

The main magnet 160 generates a main magnetic field for magnetizing atom nucleuses of elements, that is, hydrogen, phosphorous, sodium, carbon, and the like, which cause magnetic resonance phenomena among elements existing in the human body. The main magnet 160 may be a superconducting electromagnet or a permanent magnet.

The gradient coil 150 generates a spatially-linear gradient magnetic field to produce MRI images. In general, three gradient coils are used in the MRI images, each of which produces a gradient magnetic field in each of an x direction, a y direction, and a z direction. The gradient coil 150 spatially controls a rotation frequency or a phase of a magnetization vector when the magnetization vector rotates on a transverse plane, thereby indicating an MRI signal in a spatial frequency area, that is, a k area.

Magnetization vectors need to be arranged on the transverse plane in order to generate an MRI signal. To this end, the volume-type RF coil device 140 and the RF coil assembly 130 which generate an RF magnetic field where a Larmor frequency is a main frequency are required. The volume-type RF coil device 140 and the RF coil assembly 130, to which an RF current in a Larmor frequency band is applied, generate a rotating magnetic field that rotates in the Larmor frequency. When resonance of the magnetization vectors, that is, nuclear magnetic resonance (NMR), is produced due to the rotating magnetic field, the magnetization vectors are arranged on the transverse plane. Once the magnetization vectors are arranged on the transverse plane, the magnetization vectors rotating on the transverse plane in the Larmor frequency produce an electromotive force in the volume-type RF coil element 140 and the RF coil assembly 130 according to Faraday's law. When electromotive signals, that is, received RF signals, are amplified by a high frequency amplifier and then demodulated by a sine wave of the Larmor frequency, magnetic resonance signals in a base band may be obtained. The magnetic resonance signals in the base band are transmitted to the computing device 100, and an MRI image is produced by an image processor 120 through processes such as quantization.

A general principle for generating an MRI image by using the MRI system 10 has been briefly described. A process of generating an MRI image would have been obvious to one of ordinary skill in the art, and thus a detailed description thereof will be omitted.

In the MRI system 10, the volume-type RF coil device 140 included in the cylindrical housing 190 may be used to capture an MRI image of an entire body of the subject. Unlike the volume-type RF coil device 140, the RF coil assembly 130 placed on a body part of the subject may be used to capture an MRI image of body parts of the subject, for example, the head, the chest, legs, or the like. The RF coil assembly 130 is a separate device installed outside the cylindrical housing 190 and may be moved and placed on a body part of the subject which is desired to be captured through the MRI.

A birdcage coil, a saddle coil, a transverse electromagnetic (TEM) coil, an Rx only surface coil, etc. are well known as RF coils installed on a body part of the subject. However, the aforementioned RF coils have different structures from the RF coil assembly 130 according to the present embodiment.

As described above, FIG. 1A shows the RF coil assembly 130 having the planar structure, whereas FIG. 1B shows the RF coil assembly 130 having a cylindrical structure. However, functions and roles of the RF coil assembly 130 of FIGS. 1A and 1B are the same.

Resonance frequencies operating in the MRI system 10 may vary. When the MRI system 10 operates at 3 teslas (3 T), the MRI system 10 has an operating frequency of 127.74 MHz. When the MRI system 10 operates at 4.7 T, an operating frequency of the MRI system 10 is 200 MHz. When the MRI system 10 operates at 7 T, an operating frequency of the MRI system 10 is 300 MHz. When the MRI system 10 operates at 9.4 T, an operating frequency of the MRI system 10 is 400 MHz.

Figure 2:
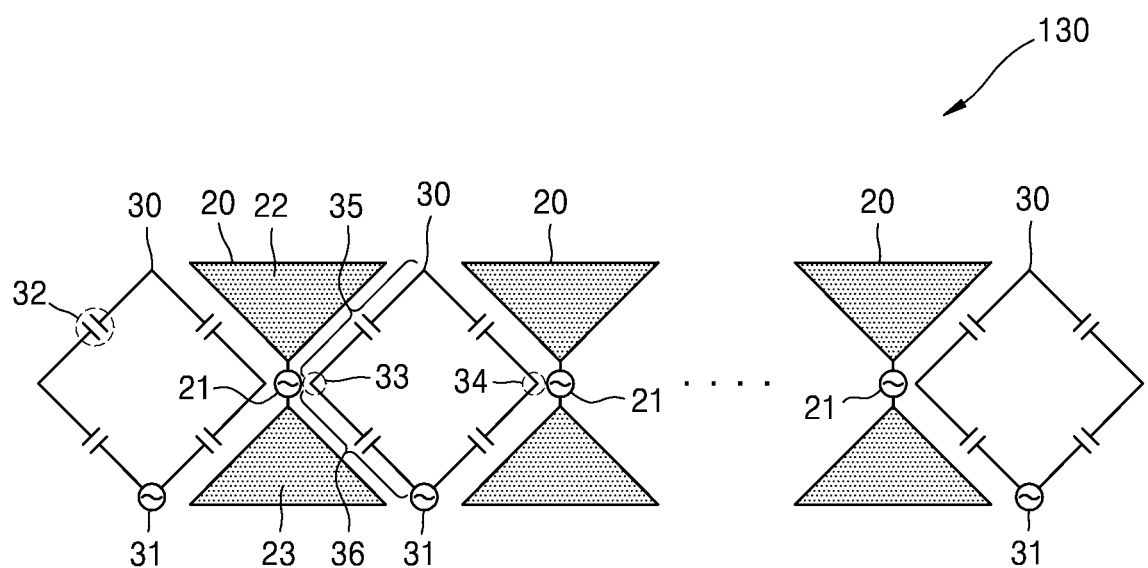
FIG. 2 shows an example of a radio frequency (RF) coil assembly 130 according to an embodiment.

FIG. 2 shows an example of an RF coil assembly 130 according to an embodiment.

Referring to FIG. 2, the RF coil assembly 130 includes a bow-tie antenna 20 and a loop coil 30.

The RF coil assembly 130 according to an embodiment may include bow-tie antennas 20 and loop coils 30. As shown in FIG. 2, the bow-tie antennas 20 and the loop coils 30 may be alternately aligned. The bow-tie antennas 20 and the loop coils 30 may be adjacent to one another. The bow-tie antennas 20 and the loop coils 30 may be aligned in a row. The bow-tie antennas 20 may each be between the loop coils 30, and the loop coils 30 may each be between the bow-tie antennas 20. The bow-tie antennas 20 and the loop coils 30 may be aligned in a horizontal direction on the same plane.

A bow-tie antenna may be a dipole antenna having two poles that are symmetrically aligned and may have a shape similar to a bow tie. The bow-tie antenna may be a broadband antenna having a broad frequency band and may generate a traveling wave.

For example, the bow-tie antenna 20 includes two triangle portions 21 and 22 that are symmetrical to each other. FIG. 2 shows that the triangle portions 21 and 22 have surface structures, but the present disclosure is not limited thereto. Vertices of the triangle portions 21 and 22 may point to central portions of the bow-tie antennas 20.

The loop coil 30 may be polygonal. The loop coil 30 may include at least one vertex or at least one line segment. The loop coil 30 may include a capacitor 32 for adjusting a resonance frequency. The loop coils 30 of FIG. 2 are apart from one another and thus are decoupled well so that additional decoupling may not be necessary. However, the present disclosure is not limited thereto. Each loop coil 30 may further include a capacitor (not shown) for additional decoupling around a vertex that is the closest to an adjacent loop coil.

As shown in FIG. 2, in a structure in which the loop coil 30 is close to the bow-tie antenna 20, a vertex of the loop coil 30 may point to the central portion of the bow-tie antenna 20. As shown in FIG. 2, when the bow-tie antennas 20 are arranged around both sides of the loop coil 30, vertices 33 and 34 of the loop coil 30 may respectively point to central portions of the bow-tie antennas 20 arranged around the sides of the loop coil 30.

Referring to FIG. 2, the loop coil 30 may include a line segment 35 that is parallel to an edge of the triangle portion 22 of the bow-tie antenna 20. For example, the bow-tie antenna 20 may include the first triangle portion 22 and the second triangle portion 23, and the loop coil 30 may include the first line segment 35 that is parallel to an edge of the first triangle portion 22 and a second line segment 36 that is parallel to an edge of the second triangle portion 23. A vertex 33 between the first line segment 35 and the second line segment 36 may point to a central portion (i.e., the central portion of the bow-tie antenna 20) between the first triangle portion 22 and the second triangle portion 23.

Referring to FIG. 2, the loop coil 30 having a rhombus structure and the bow-tie antenna 20 having a triangle structure may form the RF coil assembly 130 without gaps. Referring to FIG. 2, the loop coils 30 have a rhombus structure and are not close to other loop coils 30, and the bow-tie antenna 20 is between the loop coils 30. Thus, compared to a structure of an RF coil assembly that only includes loop coils 30, the RF coil assembly 130 has great decoupling performance.

Referring to FIG. 2, in the RF coil assembly 130, the loop coils 30 are apart from each other, and vertices of the loop coils 30 having rhombus structures are close to each other so that the RF coil assembly 130 has great decoupling performance. In addition, as the bow-tie antennas 20 (in detail, triangle portions of the bow-tie antennas 20) are arranged between the loop coils 30, gaps that may be formed between the loop coils 30 and the bow-tie antennas 20 on a plane are reduced, and thus the sensitivity and homogeneity in the B1 field may be great.

Referring to FIG. 2, the bow-tie antennas 20 and the loop coils 30 may be respectively connected to channels 21 and 31 and may receive/transmit signals. FIG. 2 shows that the channels 21 and 31 connected to the bow-tie antennas 20 and the loop coils 30 receive/transmit alternating current (AC) signals. However, the present disclosure is not limited thereto.

The number of bow-tie antennas 20 and the number of loop coils 30 of the RF coil assembly 130 are not limited to those shown in FIG. 2 and may vary according to the user of the RF coil assembly 130 and designs of the MRI system 10.

The RF coil assembly 130 may operate in a transmission mode, in which an RF signal is transmitted, or a receiving mode in which a magnetic resonance signal resulting from excitation by the RF signal and generated from the subject is received. The RF coil controller 110 of FIG. 1 may control an operation mode of the RF coil assembly 130.

The bow-tie antenna 20 may be a transmit-only antenna operating only in the transmission mode. The loop coil 30 may be a transmission/receiving coil operating either in the transmission mode or the receiving mode. The loop coil 30 may operate only in the receiving mode.

For example, the RF coil controller 110 may drive the bow-tie antennas 20 when the RF coil assembly 130 is in the transmission mode and may drive the loop coils 30 when the RF coil assembly 130 is in the receiving mode. In this case, the bow-tie antennas 20 transmit RF signals, and the loop coils 30 receive magnetic resonance signals resulting from excitation by the RF signals and generated from the subject.

Alternatively, the RF coil controller 110 may drive the bow-tie antennas 20 and the loop coils 30 when the RF coil controller 110 is in the transmission mode and may drive the loop coils 30 when the RF coil assembly 130 is in the receiving mode. In this case, the bow-tie antennas 20 and the loop coils 30 transmit RF signals, and the loop coils 30 receive magnetic resonance signals resulting from excitation by the RF signals and generated from the subject.

When the MRI system 10 operates in an ultra high magnetic field at at least 7 T and the RF coil assembly 130 includes Tx/Rx loop coils, homogeneity of a B1 magnetic field generated by the Tx/Rx loop coils may decrease.

Accordingly, the MRI system 10, that is, the RF coil assembly 130, separates Tx only coils from Rx only coils so as to increase the homogeneity of the B1 magnetic field generated by the RF coil assembly 130 even in the ultra high magnetic field of at least 7 T. For example, the bow-tie antennas 20 may be used only for transmission, and the loop coils 30 may be used only for reception.

As intensity of the magnetic field of the MRI system 10 increases, a length of an RF wavelength decreases. Thus, when Tx/Rx coils having a single channel are used, it is difficult to uniformly obtain images, and accordingly it is required to use coils having multiple channels.

The bow-tie antennas 20 and the loop coils 30 of FIG. 2 may be mutli-channel phased array antennas. In the transmission mode, the bow-tie antennas 20 may generate traveling waves, and the loop coils 30 may generate standing waves. By using RF coils of multi-channel antennas, images may be uniformly produced even in an ultra high magnetic field. Also, in the case of standing waves, homogeneity of a B1 field decreases in an ultra high magnetic field, but as the bow-tie antennas 20 according to an embodiment generate traveling waves, the B1 field may become uniform.

MODE OF THE INVENTION

Figure 3:
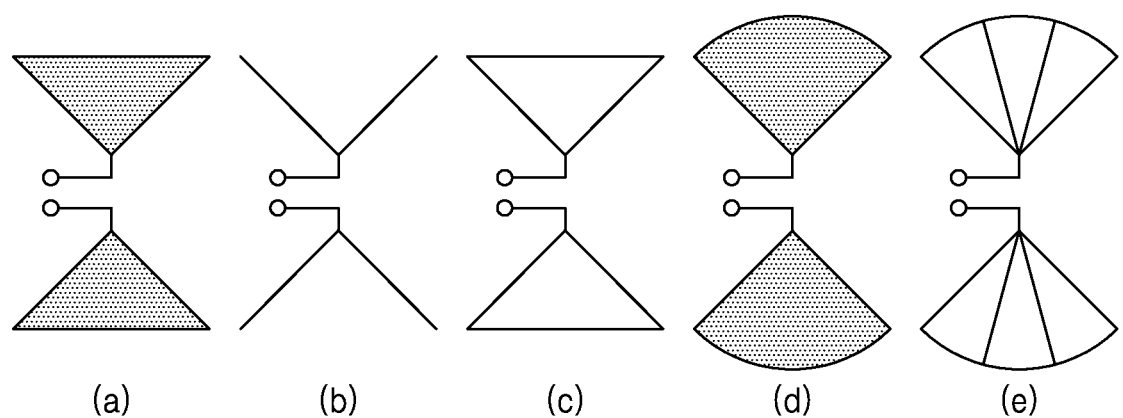
FIG. 3 shows various structures of a bow-tie antenna 20 according to an embodiment.

FIG. 3 shows various structures of the bow-tie antenna 20 according to an embodiment. FIG. 2 shows that the triangle portions 21 and 22 of the bow-tie antenna 20 have surface structures, but the present disclosure is not limited thereto. The triangle portions 21 and 22 of the bow-tie antenna 20 may have various structures.

Referring to FIG. 3A, the bow-tie antenna 20 may include triangle portions having surface structures. Referring to FIG. 3B, the bow-tie antenna 20 may include triangle portions defined by two line segments that form a certain angle from a central portion of the bow-tie antenna 20. Referring to FIG. 3C, the bow-tie antenna 20 may include loop-shaped triangle portions. Referring to FIG. 3D, the bow-tie antenna 20 may include sector-shaped triangle portions having surface structures. Referring to FIG. 3E, the bow-tie antenna 20 may include triangle portions defined by line segments, which are radially arranged from the central portion of the bow-tie antenna 20, and arcs connected to the line segments. In the present embodiment, a structure of the bow-tie antenna 20 is not limited to a certain structure.

Figure 4:
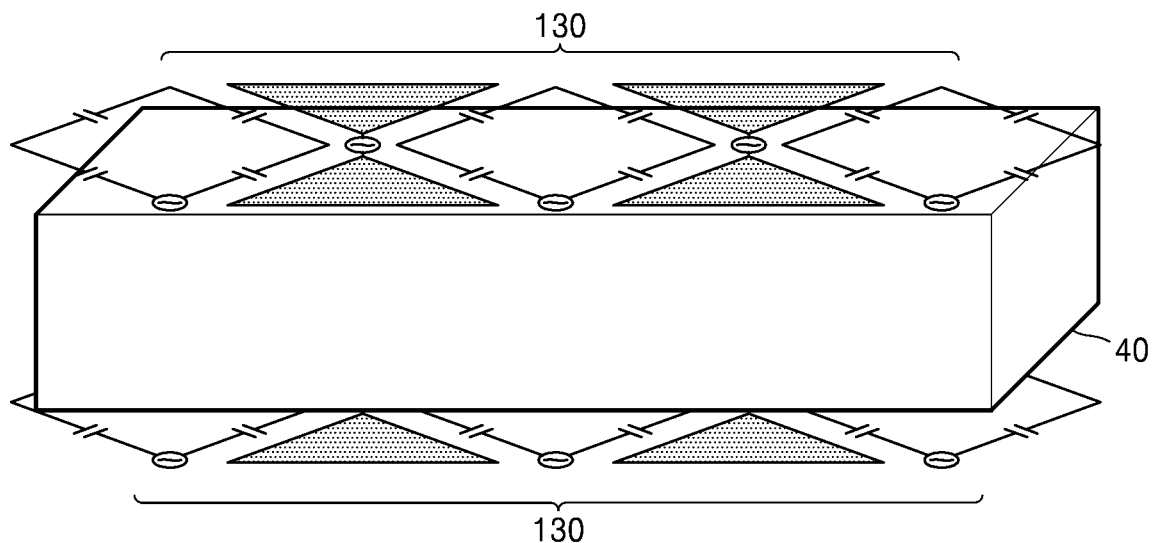
FIG. 4 shows an example in which the RF coil assemblies 130 have planar structures, according to an embodiment.

FIG. 4 shows an example in which the RF coil assemblies 130 have planar structures, according to an embodiment. Referring to FIG. 4, the RF coil assemblies 130 according to an embodiment are placed on and under a subject 40 and thus may transmit an RF signal to the subject 40 or receive a magnetic resonance signal from the subject 40. Although FIG. 4 shows that the RF coil assemblies 130 are placed on and under the subject 40, the RF coil assemblies 130 may be placed at various locations to surround the subject 40.

Figure 5:
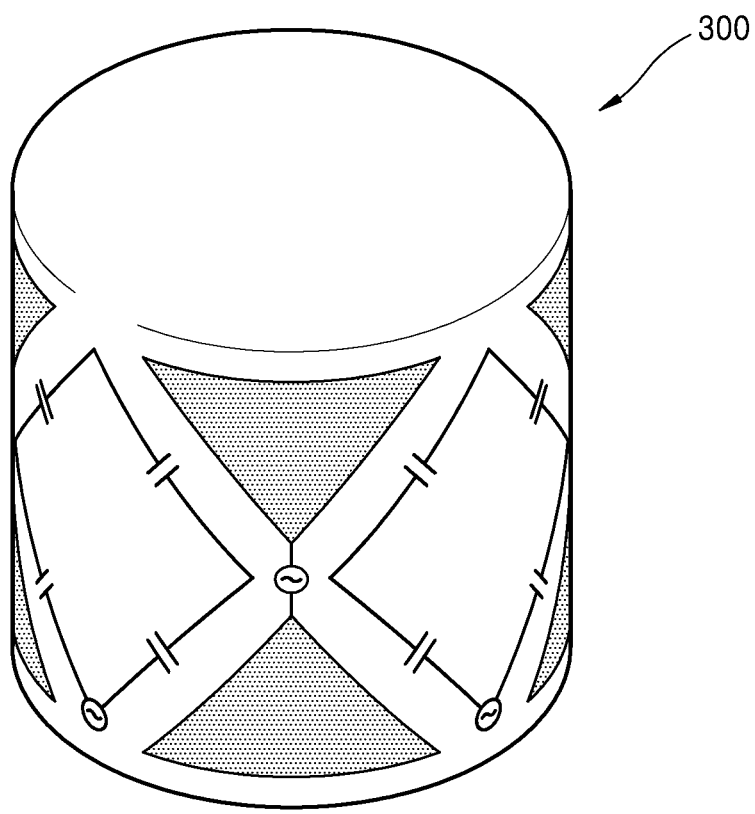
FIG. 5 shows an example in which the RF coil assembly 130 has a cylindrical structure, according to an embodiment.

FIG. 5 shows an example in which the RF coil assembly 130 has a cylindrical structure, according to an embodiment. Referring to FIG. 5, a structure of the RF coil assembly 130 of FIG. 2 may surround a surface of the cylindrical structure. The RF coil assembly 130 having a cylindrical structure may surround the subject 40.

Figure 6:
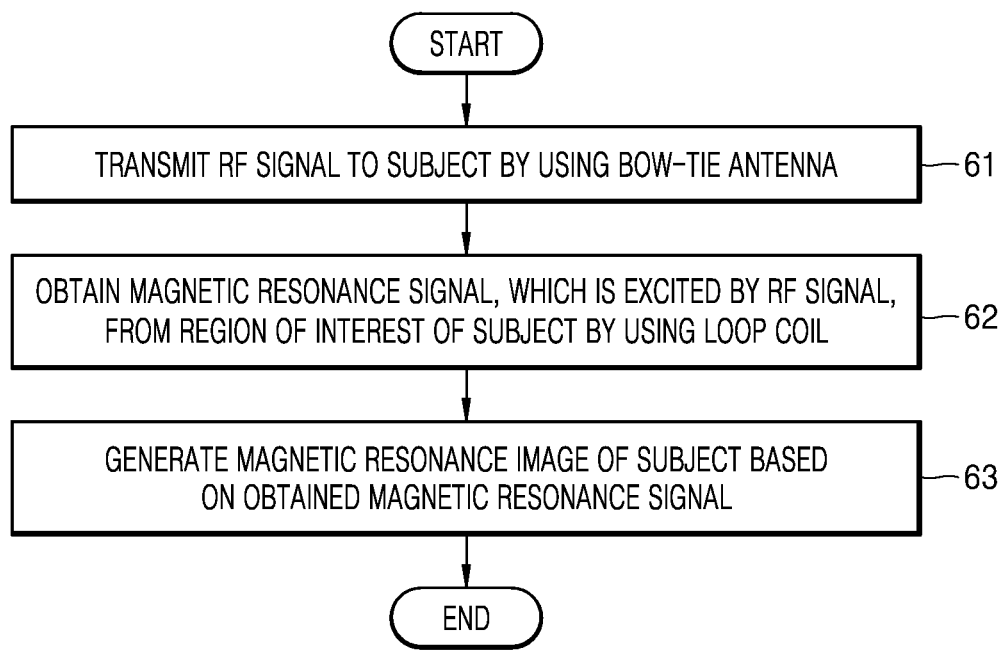
FIG. 6 is a flowchart of a method of generating an image of an MRI system according to an embodiment.

FIG. 6 is a flowchart of a method of generating an image of the MRI system 10 according to an embodiment. The flowchart of FIG. 6 includes processes that are time-serially performed in the MRI system 10 of FIG. 1. Therefore, although not repeatedly provided, the descriptions of the components with reference to FIG. 1 will be applied to FIG. 6.

Referring to FIG. 6, in operation 61, the RF coil controller 110 transmits an RF signal to the subject by using the bow-tie antenna 20. The RF coil assembly 130 controlled by the RF coil controller 110 includes the bow-tie antenna 20 and the loop coil 30. The loop coil 30 operates in a transmission mode, in which an RF signal is transmitted, or a receiving mode, in which a magnetic resonance signal resulting from excitation by the RF signal is received from the subject, and the bow-tie antenna 20 operates in the transmission mode. When the loop coil 30 operates both in the transmission mode and the receiving mode, the RF coil controller 110 may transmit the RF signal to the subject by using the bow-tie antenna 20 and the loop coil 30 in operation 61.

In operation 62, the RF coil controller 110 obtains the magnetic resonance signal, which results from excitation by the RF signal, from the region of interest of the subject by using the bow-tie antenna 20 and the loop coil 30.

In operation 63, the image processor 120 generates a magnetic resonance image of the subject based on the magnetic resonance signal obtained by using the loop coil 30.

The method of generating the image according to the embodiment of FIG. 6 may be written as programs executable by computers and may be implemented in general-use digital computers that execute the programs using a computer-readable recoding medium. Examples of the computer-readable recoding medium include magnetic storage media (e.g., read only memory (ROM), floppy disks, hard disks, etc.), optical recording medium (e.g., CD-ROMs, DVDs, etc.).

In the RF coil assembly 130, a desired B1 field may be implemented in a region of interest by variously setting the number, shapes, locations, etc. of loop coils and bow-tie antennas. When the number of channels is limited when setting the number of loop coils and bow-tie antennas, loop coils and bow-tie antennas may be connected to one channel.

While this present disclosure has been particularly shown and described with reference to embodiments thereof, it will be understood by those skilled in the art that various changes in form and details may be made therein without departing from the spirit and scope of the present disclosure as defined by the appended claims. The embodiments should be considered in descriptive sense only and not for purposes of limitation. Therefore, the scope of the present disclosure is defined not by the detailed description of the present disclosure but by the appended claims, and all differences within the scope will be construed as being included in the present disclosure.

INDUSTRIAL APPLICABILITY

The present disclosure may be applied to a radio frequency (RF) coil for magnetic resonance imaging (MRI), an MRI system, and a method of generating an image of the MRI system.

The present disclosure has been described with reference to embodiments thereof. Numerous modifications and adaptations will be readily apparent to one of ordinary skill in the art without departing from the spirit and scope of the present disclosure.

The invention claimed is:

1. A radio frequency (RF) coil for magnetic resonance imaging (MRI), the RF coil comprising:
    a bow-tie antenna having two triangular portions that are symmetrical to each other; and
    a loop coil having a vertex,
    wherein the bow-tie antenna is spaced apart from the loop coil,
    vertices of the two triangular portions and the loop coil taper to a central portion of the bow-tie antenna, and
    the bow-tie antenna and the loop coil are aligned in a horizontal direction on a same plane.

2. The RF coil of claim 1, wherein the RF coil comprises a plurality of loop coils, and the bow-tie antenna is between the plurality of loop coils.

3. A radio frequency (RF) coil for magnetic resonance imaging (MRI), the RF coil comprising:
    a plurality of bow-tie antennas each having two triangular portions that are symmetrical to each other; and
    a plurality of loop coils each having a vertex,
    wherein each of the plurality of bow-tie antennas is disposed between adjacent ones of the plurality of loop coils,
    respective ones of the plurality of bow-tie antennas and the plurality of loop coils are aligned and alternately disposed, vertices of the two triangular portions and the loop coil taper to a central portion of the bow-tie antenna, and
    each of the plurality of bow-tie antennas and the loop coil are aligned in a horizontal direction on a same plane.

4. The RF coil of claim 1, wherein the loop coil is polygonal,
    the loop coil is close to the bow-tie coil.

5. The RF coil of claim 4, wherein the RF coil comprises a plurality of bow-tie antennas,
    the loop coil is between the plurality of bow-tie antennas, and
    vertices of the loop coil respectively point to central portions of the plurality of bow-tie antennas arranged around sides of the loop coil.

6. The RF coil of claim 1, wherein the loop coil is adjacent to the bow-tie coil and is parallel to an edge of one of the two triangular portions.

7. The RF coil of claim 6, wherein the bow-tie antenna comprises a first triangular portion and a second triangular portion, the loop coil comprises a first line segment parallel to an edge of the first triangular portion and a second line segment parallel to an edge of the second triangular portion, and
a vertex between the first and second line segments points to the central portion of the bow-tie antenna.

8. The RF coil of claim 1, wherein the bow-tie antenna transmits an RF signal, and
    the loop coil receives, from a subject, a magnetic resonance signal resulting from excitation by the RF signal.

9. The RF coil of claim 8, wherein the loop coil operates in a transmission mode in which the RF signal is transmitted or in a receiving mode in which the magnetic resonance signal resulting from the excitation by the RF signal is received from the subject.

10. The RF coil of claim 1, wherein each of the bow-tie antenna and the loop coil is connected to an RF channel.

11. A magnetic resonance imaging (MRI) system comprising:
    a radio frequency (RF) coil configured to transmit an RF signal to a subject and obtain a magnetic resonance signal from a region of interest of the subject, the magnetic resonance signal resulting from excitation by the transmitted RF signal;
    an RF coil controller configured to an RF transmission mode and an RF receiving mode of the RF coil; and
    an image processor configured to generate an MRI image of the subject based on the obtained magnetic resonance signal,
    wherein the RF coil comprises a bow-tie antenna having two triangular portions that are symmetrical to each other and a loop coil having a vertex, the bow-tie antenna is spaced apart from the loop coil, vertices of the two triangular portions and the loop coil taper to a central portion of the bow-tie antenna, and
    the bow-tie antenna and the loop coil are aligned in a horizontal direction on a same plane.

12. A method of generating an image of a magnetic resonance imaging (MRI) system comprising a radio frequency (RF) coil comprising a bow-tie antenna and a loop coil, the method comprising:
    transmitting an RF signal to a subject by using the bow-tie antenna;
    obtaining a magnetic resonance signal from a region of interest of the subject by using the loop coil, the magnetic resonance signal resulting from excitation by the transmitted RF signal; and
    generating an MRI image of the subject based on the obtained magnetic resonance signal,
    wherein the bow-tie antenna is spaced apart from the loop coil, the bow-tie antenna has two triangular portions that are symmetrical to each other, vertices of the two triangular portions and the loop coil taper to a central portion of the bow-tie antenna, and
    the bow-tie antenna and the loop coil are aligned in a horizontal direction on a same plane.

13. The method of claim 12, wherein the loop coil operates in a transmission mode in which the RF signal is transmitted or in a receiving mode in which the magnetic resonance signal resulting from excitation by the RF signal is received from the region of interest of the subject, and
    in the transmitting of the RF signal, the RF signal is transmitted to the subject by using the bow-tie antenna and the loop coil.

14. The RF coil of claim 2, wherein the RF coil comprises a plurality of bow-tie antennas, and the plurality of bow-tie antennas and the plurality of loop coils are alternately aligned.

\* \* \* \* \*